United States Patent [19]

Winkel et al.

[11] Patent Number: 4,744,827
[45] Date of Patent: May 17, 1988

[54] (METH)-ACRYLIC ACID DERIVATIVES OF TRICYCLODECANES AND THEIR USE

[75] Inventors: Jens Winkel, Cologne; Bruno Börner, Bergisch-Gladbach; Robert Schmitz-Josten, Cologne; Gerhard Klein, Monheim; Carlhans Süling, Odenthal; Dieter Arlt, Cologne, all of Fed. Rep. of Germany

[73] Assignee: Bayer Aktiengesellschaft, Leverkusen, Fed. Rep. of Germany

[21] Appl. No.: 870,609

[22] Filed: Jun. 4, 1986

[30] Foreign Application Priority Data

Jun. 20, 1985 [DE] Fed. Rep. of Germany ....... 3522006

[51] Int. Cl.[4] .................. A61K 6/02; C07C 69/52; C07C 125/06
[52] U.S. Cl. .................. 106/35; 260/998.11; 433/217.1; 433/226; 560/115; 560/160; 560/220
[58] Field of Search .................. 560/115, 160, 220; 106/35; 433/217.1, 226; 260/998.11

[56] References Cited

U.S. PATENT DOCUMENTS

| 4,131,729 | 12/1978 | Schmitt et al. | 526/282 |
|---|---|---|---|
| 4,172,951 | 10/1979 | Gruber et al. | 560/194 |
| 4,323,348 | 4/1982 | Schmitz-Josten et al. | 106/35 |
| 4,323,696 | 4/1982 | Schmitz-Josten et al. | 560/220 |
| 4,347,174 | 8/1982 | Nagase et al. | 260/998.11 |
| 4,379,695 | 4/1983 | Orlowski et al. | 433/217.1 |
| 4,383,826 | 5/1983 | Butler et al. | 106/35 |
| 4,420,306 | 12/1983 | Orlowski et al. | 106/35 |
| 4,605,719 | 8/1986 | Peelen | 526/282 |

FOREIGN PATENT DOCUMENTS

| 2816823 | 10/1978 | Fed. Rep. of Germany . |
|---|---|---|
| 2931926 | 2/1981 | Fed. Rep. of Germany . |
| 3135115 | 3/1983 | Fed. Rep. of Germany . |
| 3338077 | 5/1985 | Fed. Rep. of Germany . |

OTHER PUBLICATIONS

Progress in Organic Coatings, 11(1983) 297–308, Silane Adhesion Promoters in Coatings, Edwin P. Plueddemann.
Initiator–Accelerator Systems for Dental Resins, G. M. Brauer and H. Argentar, National Bureau of Standards, Washington, D.C. 20234 pp. 360–371.

Primary Examiner—Paul Lieberman
Assistant Examiner—Linda D. Skaling
Attorney, Agent, or Firm—Sprung, Horn, Kramer & Woods

[57] ABSTRACT (Meth)-acrylic acid derivatives of tricyclodecanes of the formula

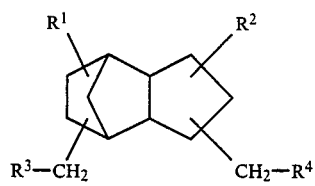

in which $R^1$ and $R^2$ are identical or different and denote hydrogen, lower alkyl, lower alkoxy, halogen or trifluoromethyl and $R^3$ and $R^4$ are identical or different and represent the group

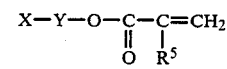

wherein X denotes a divalent bridge member from the group

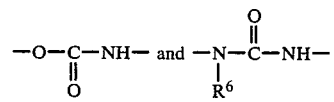

and Y denotes a divalent bridge member from the group

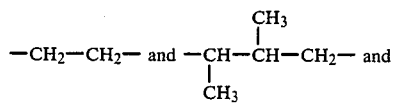

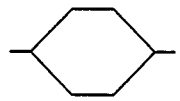

and wherein $R^5$ represents hydrogen or methyl and $R^6$ represents lower alkyl or phenyl, have been found. Dental compositions in which the present (meth)-acrylic acid derivatives of tricyclodecanes are used, exhibit considerably less polymerization shrinkage.

8 Claims, No Drawings

(METH)-ACRYLIC ACID DERIVATIVES OF TRICYCLODECANES AND THEIR USE

The invention relates to new (meth)-acrylic acid derivatives of tricyclodecanes, their preparation and their use as monomers for dental materials.

Dental compositions which contain polymerizable (meth)-acrylic acid esters of tricyclodecanes are known from DE-OS (German Published Specification) No. 2,931,926. However, these dental compositions always show polymerization shrinkage when used.

New (meth)-acrylic acid derivatives of tricyclodecanes of the formula

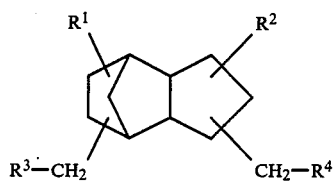

in which
  $R^1$ and $R^2$ are identical or different and denote hydrogen, lower alkyl, lower alkoxy, halogen or trifluoromethyl and
  $R^3$ and $R^4$ are identical or different and represent the group

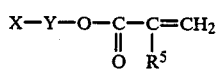

wherein
  X denotes a divalent bridge member from the group comprising

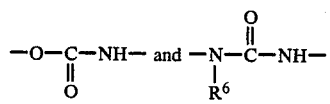

and
  Y denotes a divalent bridge member from the group comprising

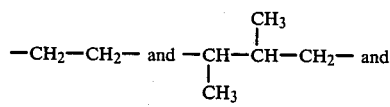

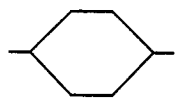

and wherein
  $R^5$ represents hydrogen or methyl and
  $R^6$ represents hydrogen, lower alkyl or phenyl,
have been found.

Surprisingly, dental compositions in which (meth)-acrylic acid derivatives of tricyclodecanes according to the invention have been used as starting materials exhibit considerably less polymerization shrinkage and are therefore particularly suitable for use in practice.

In the context of the present invention, the substituents can have the following meaning:
  Lower alkyl can denote a straight-chain or branched hydrocarbon radical with 1 to about 6 carbon atoms. The following lower alkyl radicals may be mentioned as examples: methyl, ethyl, propyl, isopropyl, butyl, isobutyl, pentyl, isopentyl, hexyl and isohexyl. The methyl and the ethyl radical are preferred.
  Lower alkoxy can denote a straight-chain or branched hydrocarbon radical which has 1 to about 6 carbon atoms and is bonded via oxygen. The following lower alkoxy radicals may be mentioned as examples: methoxy, ethoxy, propoxy, isopropoxy, butoxy, isobutoxy, pentoxy, isopentoxy, hexoxy and isohexoxy. The methoxy and the ethoxy radical are preferred.
  Halogen can denote fluorine, chlorine, bromine and iodine. Fluorine and chlorine are preferred.

Preferred (meth)-acrylic acid derivatives of tricyclodecanes of the formula I are those in which
  $R^1$ and $R^2$ denote hydrogen,
  $R^3$ and $R^4$ are identical or different and represent the group

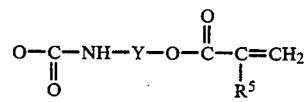

wherein
  Y denotes a divalent bridge member from the group comprising

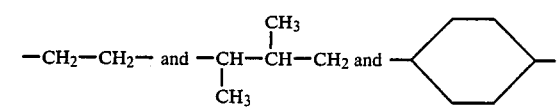

and wherein
  $R^5$ represents hydrogen or methyl.

The following (meth)-acrylic acid derivatives of tricyclodecanes may be mentioned as examples:

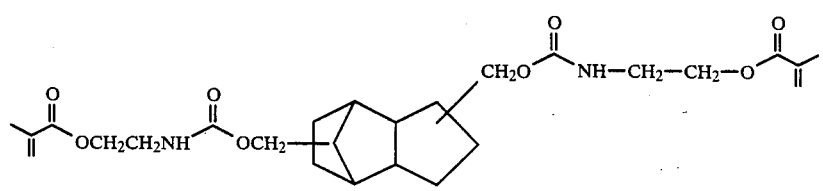

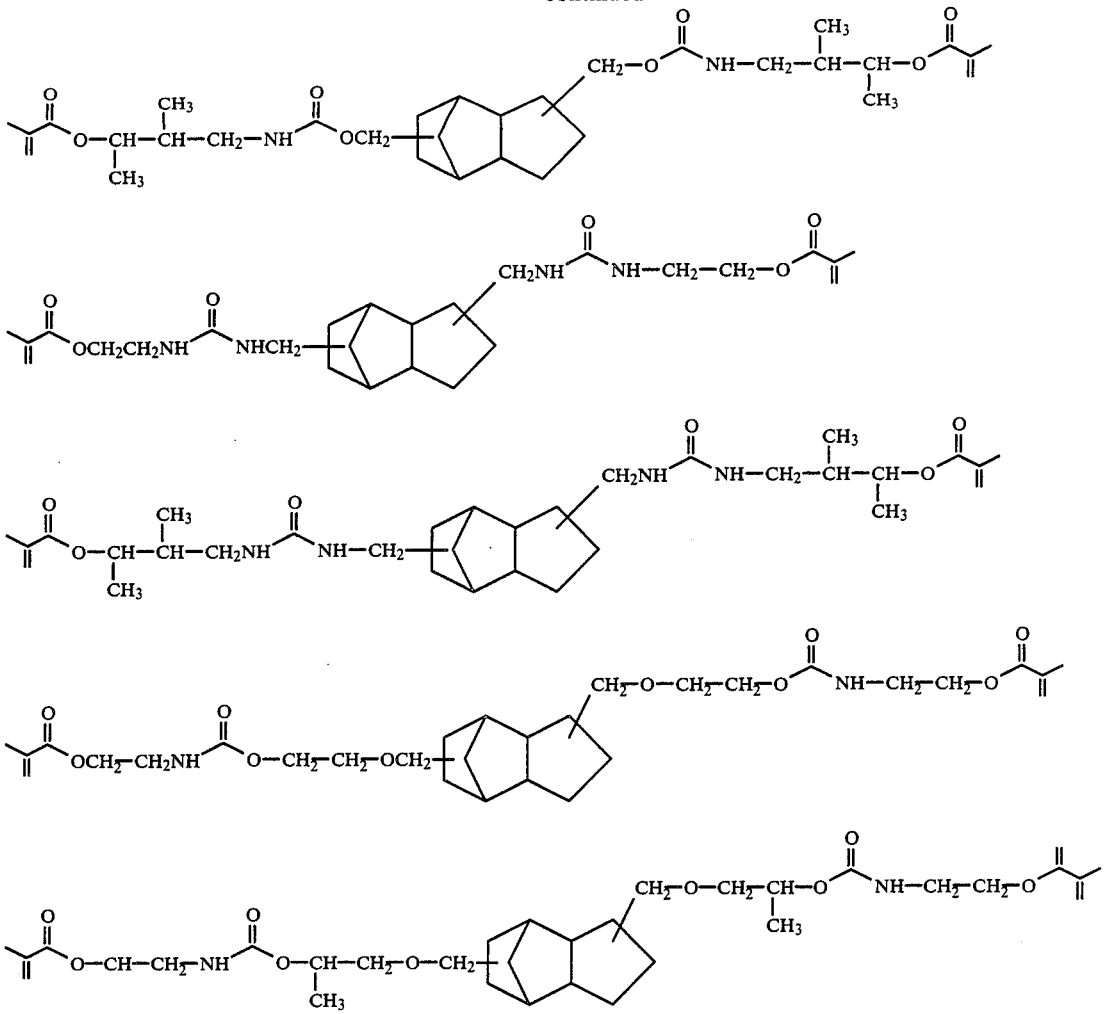

A process has also been found for the preparation of (meth)-acrylic acid derivatives of tricyclodecanes, which is characterized in that tricyclodecanes of the formula

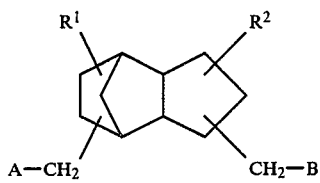

in which
R¹ and R² are identical or different and denote hydrogen, lower alkyl, lower alkoxy, halogen or trifluoromethyl and
A and B are identical or different and denote hydroxyl or the radical —NHR⁶,
wherein
R⁶ represents hydrogen, lower alkyl or phenyl, are reacted with (meth)-acrylic acid ester-isocyanates of the formula

in which
R⁵ represents hydrogen or methyl and
Y denotes a divalent bridge member from the group comprising

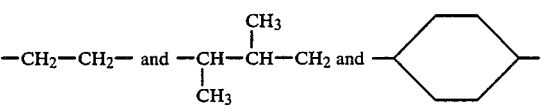

if appropriate in an inert solvent in the presence of a catalyst in the temperature range from 0° to 100° C.

The dihydroxymethyltricyclodecanes employed as starting compounds are known per se (literature: U.S. Pat. No. 4,131,729), and they can be prepared, for example, by reaction of dicyclopentadiene, formaldehyde and hydrogen.

The diaminomethyltricyclodecanes employed as starting compounds are known per se and can be prepared, for example, by reaction of tosylates with ammonia. (Meth)-acrylic acid ester-isocyanates are known from DE-OS (German Published Specification) No.

3,338,077 and can be prepared, for example, by phosgenation of dihydrooxanines.

It is possible to carry out the process according to the invention without solvents.

Inert solvents for the process according to the invention are preferably polar solvents which do not change under the reaction conditions. Preferred solvents are, in particular, chloroform, tetrahydrofuran, dioxane, methylene chloride, toluene, acetonitrile and freon Particularly preferred solvents are chloroform, tetrahydrofuran, freon and acetonitrile.

In a particular embodiment, the process according to the invention is carried out with the exclusion of water. A maximum amount of water of less than 0.1% is particularly preferred.

Catalysts for the process according to the invention are in general metal salts of higher fatty acids. Examples of preferred catalysts are dibutyl-tin laurate or tin(II) octoate. However, compounds with tertiary amino groups, such as pyridine, methylpyridine, N,N'-dimethylpiperazine and N,N-dimethylbenzylamine, and titanium compounds are also preferred.

The catalyst is in general employed in an amount of 0.01 to 2.5% by weight, preferably 0.1 to 1.5% by weight, based on the total amount of the reactants.

In a preferred embodiment, the process according to the invention can be carried out in the presence of a polymerization inhibitor. A polymerization inhibitor can be, for example, 2,6-di-tert.-butyl-4-methylphenol. However, it is also possible to use oxygen as the polymerization inhibitor. In this case, oxygen is passed into the reaction mixture. In general, atmospheric oxygen is sufficient.

The polymerization inhibitor is in general employed in an amount of −0.01 to 0.2% by weight, preferably 0.05 to 0.1% by weight.

The tricyclodecanes of the formula II are in general employed in an amount of 0.8 to 1.4 moles, preferably 0.8 to 1.2 moles, per 2 moles of the (meth)-acrylic acid ester-isocyanates.

The process according to the invention is in general carried out in the temperature range from 0° to 100° C., preferably 30° to 70° C. The process according to the invention is in general carried out under normal pressure. However, it is also possible to carry out the process according to the invention under reduced or increased pressure (for example in the pressure range from 0.1 to 10 bar).

The process according to the invention can be carried out, for example, as follows:

The reactants are dissolved in the solvent, and the catalyst and, if appropriate, the polymerization inhibitor are added, with stirring. The course of the reaction with respect to time can be monitored, for example, by measurement of the IR spectra. When reaction of the isocyanate groups is complete, the reaction products are isolated by removing the solvent. Prior purification with the aid of absorbents, for example active charcoal, bleaching earth, silica gel or aluminum oxide, is possible.

The (meth)-acrylic acid derivatives of tricyclodecanes according to the invention can be used as monomers for dental materials. Thus, it is possible to employ them as monomers for polymeric dental filling compositions or coating agents (dental lacquers) in the dental field.

For use as monomers for polymeric dental filling compositions or coating agents in the dental field, the (meth)-acrylic acid derivatives of tricyclodecanes according to the invention can be mixed with monomers which are known per se, for example in order to adapt the viscosity to suit the intended use. Viscosities in the range from 60 to 10,000 mPas are preferred here. This can be achieved, if appropriate, by admixing a comonomer of low viscosity to the monomers according to the invention, as a reactive diluent. The compounds according to the invention are employed in the mixture with comonomers in an amount of about 30 to about 90% by weight, an amount of 50 to 85% by weight being particularly preferred.

In the context of the present invention, it is likewise preferable to employ mixtures of different (meth)-acrylic acid derivatives of tricyclodecanes according to the invention.

It is also possible to employ monomer mixtures which contain several comonomers as reactive diluents.

The following comonomers may be mentioned as examples: triethylene glycol dimethacrylate, tetraethylene glycol dimethacrylate, 1,12-dodecanediol dimethacrylate, 1,6-hexanediol dimethacrylate, diethylene glycol dimethacrylate, 2,2-bis-[p-(2'-hydroxy-3'-methacrylolyloxypropoxy)-phenyl]-propane, 2,2-bis-[p-(2'-methacrylolyloxyethoxy)phenyl]-propane, trimethylolpropane tri-(meth)-acrylate and bis-(meth)-acrylolyloxyethoxymethyl-tricyclo-[5.2.1.0$^{2,6}$]-decane (DE-OS (German Published Specification) No. 2,931,925 and DE-OS (German Published Specification) No. 2,931,926).

Comonomers which have a boiling point above 100° C. under 13 mbar are particularly preferred.

The (meth)-acrylic acid derivatives of tricyclodecanes according to the invention, if appropriate mixed with the comonomers mentioned, can be hardened by methods which are known per se to give crosslinking polymers (Am. Chem.Soc., Symp.Ser. 212, 359–371 (1983)). A system of a peroxidic compound and a reducing agent, for example based on tertiary aromatic amines, is suitable for the so-called redox polymerization.

Examples of peroxides are: dibenzoyl peroxide, dilauryl peroxide and di-4-chlorobenzoyl peroxide.

Examples which may be mentioned of tertiary aromatic amines are N,N-dimethyl-p-toluidine, bis-(2-hydroxyethyl)-p-toluidine, bis-(2-hydroxyethyl)-3,5-dimethylaniline and N-methyl-N-(2-methyl-carbamoyloxypropyl)-3,5-dimethylaniline (German Patent Specification No. 2,759,239).

The concentrations of the peroxide and of the amine are advantageously chosen such that they are 0.1 to 5% by weight, preferably 0.5 to 3% by weight, based on the monomer mixture. The monomer mixtures containing peroxide and amine are stored separately until used.

The monomers according to the invention can also be brought to polymerization by irradiation with UV light or visible light (for example in the wavelength range from 230 to 650 nm). Examples of suitable initiators for the photoinitiated polymerization are benzil, benzil dimethyl ketal, benzoin monoalkyl ethers, benzophenone, p-methoxybenzophenone, fluorenone, thioxanthone, phenanthrenequinone and 2,3-bornanedione (camphorquinone), if appropriate in the presence of photoactivators with a synergistic action, such as N,N-dimethylaminoethyl methacrylate, triethanolamine or 4-N,N-dimethylaminobenzenesulphonic acid diallylamide. The procedure for the photopolymerization process is described, for example, in German Patent Specification No. 3,135,115.

In addition to the initiators described above, light stabilizers and stabilizers known per se for this intended use can be added to the (meth)-acrylic acid derivatives of tricyclodecanes according to the invention.

Light stabilizers are described, for example, in (Grächter, Müller: Kunststoff-Additive (Plastics Additives), 2nd edition, Carl Hauser Verlag, Munich, Vienna). The following light stabilizers may be mentioned as examples: Cyasorbuva ®, Tinuvin P ®, Tinuvin 770 ®, Tinuvin 622 ® and Tinnvin 765 ®.

Stabilizers are described, for example, in (Ullmanns Encyclopädie der technischen Chemie (Ullmann's Encyclopaedia of Industrial Chemistry), Verlag Chemie Weinheim, 4th edition, Volume 8). The following stabilizers may be mentioned as examples: 2,6-di-tert.-butylphenol, 2,6-di-tert.-butyl-4-methylphenol, 2,6-di-octadecyl-4-methylphenol, 1,1'-methylene-bis-(naphth-2-ol) and the like.

The light stabilizer and the stabilizer are in each case in general employed in an amount of 0.01 to 0.50 parts by weight per 100 parts by weight of the monomer mixture.

The monomer mixtures can be employed, without the addition of fillers, as coating agents (dental lacquers).

When used as dental filling compositions, fillers are in general added to the monomer mixtures obtained. Monomer mixtures which have a viscosity in the range from 60 to 10,000 mPas are particularly advantageous, in order to achieve a high degree of filling.

Inorganic fillers are preferably admixed to the monomer mixtures containing the compounds according to the invention. Examples of inorganic fillers which may be mentioned are rock crystal, graphite, cristoballite, quartz glass, highly disperse silicic acid, aluminium oxide and glass ceramics, for example glass ceramics containing lanthanum and zirconium (DE-OS (German Published Specification) No. 2,347,501).

The inorganic fillers are preferably pretreated with an adhesion promoter to improve the bonding to the polymer matrix, for example of a polymethacrylate. Adhesion promotion can be achieved, for example, by treatment with organosilicon compounds (Progress in Organic Coatings 11 297–308 (1983)). 3-Methacrylolyloxipropyltrimethyloxysilane is preferably employed.

The fillers for the dental filling compositions according to the invention in general have an average particle diameter of 0.01 to 100 μm, preferably 0.05 to 50 μm and particularly preferably 0.05 to 5 μm. It may also be advantageous to employ several fillers of different particle diameter side by side.

The filler content in the dental filling composition is in general 5 to 85% by weight, preferably 50 to 80% by weight.

For the preparation of the dental filling compositions, the components are processed using commercially available kneading machines.

The content of (meth)-acrylic acid derivatives of tricyclodecanes according to the invention in the filling compositions is in general 5 to 85% by weight, preferably 15 to 50% by weight, based on the filling composition.

Dental materials based on the (meth)-acrylic acid derivatives of tricyclodecanes according to the invention have, surprisingly, a low polymerization shrinkage and a high mechanical strength.

PREPARATION EXAMPLES

(1) Reaction of 3(4),8(9)di-hydroxymethyl-tricyclo-[5.2.1.0$^{2,6}$]-decane with 2-isocyanatoethyl methacrylate 0.3 mole of 3(4),8(9)di-hydroxymethyl-tricyclo-[5.2.1.0$^{2,6}$]-decane, 0.6 mole of 2-isocyanatoethyl methacrylate, 0.2 g of dibutyl-tin dilaurate and 50 mg of 2,6-di-tert.-butyl-4-methyl-phenol (Ionol) are reacted in a suitably equipped reaction vessel in the course of 3 hours at 70° C., while stirring and passing through dry air. 151 g of a colourless, slightly viscous liquid are obtained.

$^1$H-NMR (ppm) in CDCl$_3$/TMS: 0.75–2.70 (14H); 1.95 (4H), 3.30–3.60 (4H); 3.70–3.95 (4H), 4.10–4.30 (4H); 50–530 (2H); 5.50–5.65 (2H) and 6.08–6.15 (2H)

Viscosity (25° C.): 885 Pas.

(2) Reaction of 3(4),8(9)di-hydroxymethyl-tricyclo-[5.2.1.0$^{2,6}$]-decane with 1-isocyanato-2-methyl-but-3-yl acrylate 0.25 mole of 3(4),8(9)-dihydroxymethyl-tricyclo-[5.2.1.0$^{2,6}$]-decane, 0.5 mole of 1-isocyanato-2-methyl-but-2-yl acrylate, 0.2 g of dibutyl-tin dilaurate and 50 mg of Ionol are reacted as described in 1.

$^1$H-NMR (ppm) in CDCl$_3$/TMS: 0.85–1.05 (6H), 1.15–1.35 (6H), 0.75–2.70 (14H), 2.70–3.55 (4H), 3.70–3.95 (4H), 4.70–5.30 (4H) and 5.70–6.55 (6H)

Viscosity (25° C.): 1,220 Pas.

USE EXAMPLES (3) Measurement of the polymerizatiion shrinkage:

2% of benzoyl peroxide is dissolved in the pure monomer. 5 g of this solution are introduced into a cylindrical glass vessel of 3 cm diameter and covered with a layer of nitrogen. The solution is heated at 80° C. for 1 hour and at 130° C. for 15 minutes, whereupon the monomers polymerize. The density of the resulting test pieces is determined and the polymerization shrinkage is determined by comparison with the density of the liquid monomers.

TABLE I

| | Polymerization shrinkage |
|---|---|
| Monomer of the comparison experiments | |
| 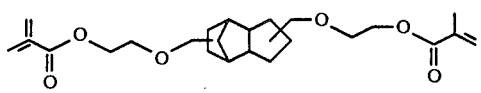 | 7.3% |
| (DE-OS (German Published Specification) 2,931,926) | |

TABLE I-continued

| | Polymerization shrinkage |
|---|---|
| 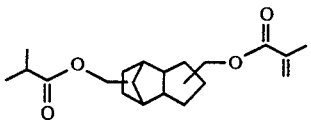 | 7.7% |
| (DE-OS (German Published Specification) 2,816,823) | |
| Monomers according to the invention | |
| 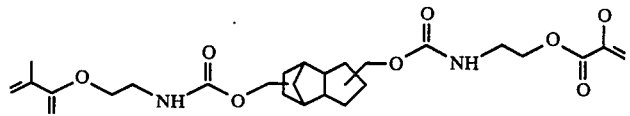 | 6.1% |
| 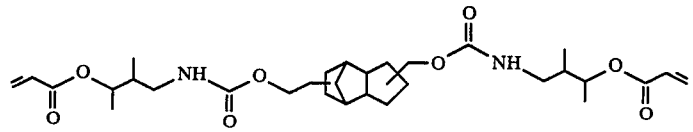 | 5.7% |

(4) Composition for filling hollow dental cavities (a) Redox-hardening system
Peroxide paste
2% of benzoyl peroxide is dissolved in a mixture of 70 parts of monomer from 1 and 30 parts of triethylene glycol dimethacrylate.
10 g of silanized radicals glass ceramic are processed with 4 g of this solution to give a paste.
Amine paste
1.4% of N-methyl-N-β-(methylcarbamyloxy)-propyl-3,5-dimethylaniline are dissolved in a mixture of 70 parts of monomer from 1 and 30 parts of triethylene glycol dimethacrylate.
4 g of this solution are processed with 10 g of silanized glass ceramic to give a paste.
If equal parts of amine paste and peroxide paste are mixed with one another, the mixture hardens in 2 minutes. The pastes can be coloured with pigment and are suitable for filling hollow dental cavities.

(b) Photo-hardening system
0.5% of N,N-diallyl-p-dimethylaminobenzenesulphonic acid amide, 0.2% of camphorquinone and 0.125% of 4-N,N-dimethylaminobenzenesulphonic acid diallylamide are dissolved in a mixture of 70 parts of monomer from 1 and 30 parts of triethylene glycol dimethacrylate. 10 g of silanized glass ceramic are processed with 4 g of this solution to give a paste. If this composition is irradiated with a commercially available dental lamp (Translux, Kulzer), a layer of 7.9 mm has hardened completely after 40 seconds.

(5) Preparation of sealer solutions (a) Redox-hardening system
Catalyst solution
2% of benzoyl peroxide are dissolved in a mixture of 10 parts of triethylene glycol dimethacrylate and 90 parts of monomer from 2.
Activator solution
2% of N-methyl-N-(methylcarbamoyloxy)-propyl-3,5-dimethylaniline are dissolved in a mixture of 10 parts of triethylene glycol dimethacrylate and 90 parts of monomer from 2.

A mixture of equal parts of catalyst solution and activator solution hardens in 1 minute 15 seconds.

(6) Photo-hardening sealer
0.5% of N,N-diallyl-p-dimethylaminobenzenesulphonic acid amide, 0.2% of camphorquinone and 0.125% of benzil dimethyl ketal are dissolved in the monomer from 1. On irradiation with a commercially available dental lamp (Translux, Kulzer), the liquid hardens to a solid film.

What is claimed is:
1. A (Meth)-acrylic acid derivative of a tricyclodecane of the formula

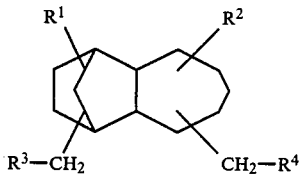

in which
R¹ and R² each independently denote hydrogen, lower alkyl, lower alkyoxy, halogen or trifluoromethyl and
R³ and R⁴ each independently represent the group

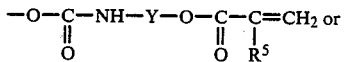

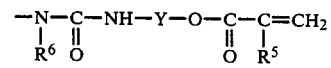

wherein
Y denotes a divalent bridge member selected from the group consisting of

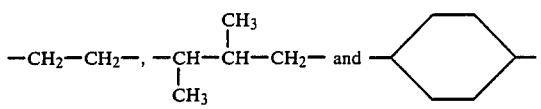

and wherein
$R^5$ represents hydrogen or methyl and
$R^6$ represents, lower alkyl or phenyl.

2. A (Meth)-acrylic acid derivative of a tricyclodecane according to claim 1,
wherein
$R^1$ and $R^2$ denote hydrogen,
$R^3$ and $R^4$ each independently represent the group

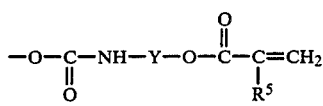

wherein
Y denotes a divalent bridge member selected from the group consisting of

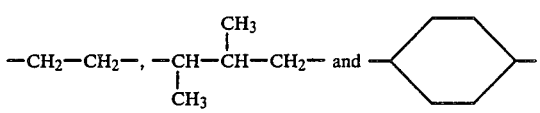

and wherein
$R^5$ represents hydrogen or methyl.

3. A process for the preparation of a (meth)-acrylic acid derivative of tricyclodecane wherein a tricyclodecane of the formula

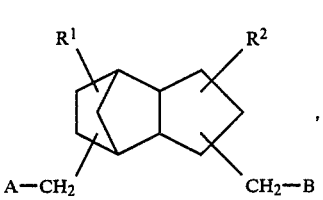

in which
$R^1$ and $R^2$ each independently denote hydrogen, lower alkyl, lower alkoxy, halogen or trifluoromethyl and
A and B each independently denote hydroxyl or the radical —$NHR^6$,
wherein
$R^6$ represents lower alkyl or phenyl, is reacted with a (meth)-acrylic acid ester-isocyanate of the formula

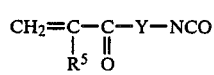

in which
$R^5$ represents hydrogen or methyl and Y denotes a divalent bridge member selected from the group consisting of

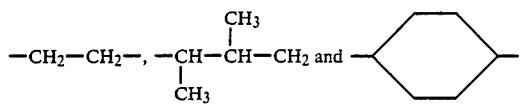

in the presence of a catalyst in the temperature range from 0° to 100° C.

4. A polymer of (meth)-acrylic acid derivatives of tricyclodecanes of the formula

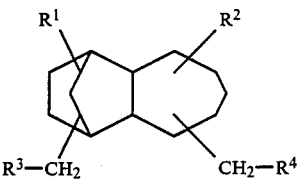

in which
$R^1$ and $R^2$ denote hydrogen, lower alkyl, lower alkoxy, halogen or trifluoromethyl and
$R^3$ and $R^4$ each independently represent the group

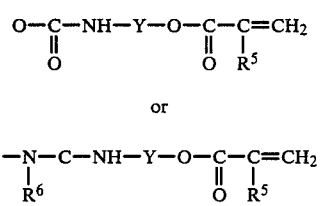

or $$-\underset{R^6}{N}-\underset{O}{\overset{\parallel}{C}}-NH-Y-O-\underset{O}{\overset{\parallel}{C}}-\underset{R^5}{\overset{|}{C}}=CH_2$$

wherein
Y denotes a divalent bridge member selected from the group consisting of

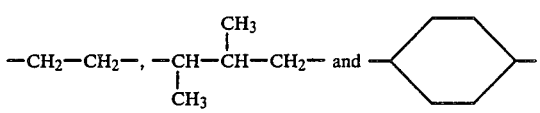

and wherein
$R^5$ represents hydrogen or methyl and
$R^6$ represent lower alkyl or phenyl.

5. A dental filling composition, comprising (meth)-acrylic acid derivatives of tricyclodecanes of the formula

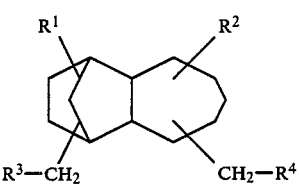

in which
$R^1$ and $R^2$ each independently denote hydrogen, lower alkyl, lower alkoxy, halogen or trifluoromethyl and
$R^3$ and $R^4$ each independently represent the group

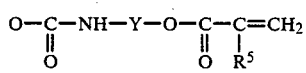

-continued or

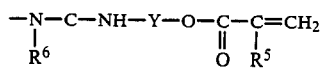

wherein

Y denotes a divalent bridge member from the group

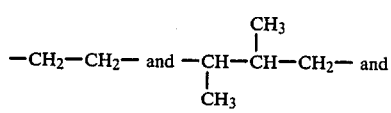

-continued

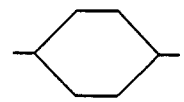

and wherein $R^5$ represent hydrogen or methyl and
$R^6$ represents lower alkyl or phenyl and 5 to 85% by weight of a suitable filler.

6. A dental filling composition according to claim 5, comprising, in addition to (meth)-acrylic acid derivatives of tricyclodecanes, another comonomer.

7. In a dental lacquer the improvement comprising (meth)-acrylic acid derivatives of tricyclodecanes according to claim 1 as the coating agent.

8. A process according to claim 3, wherein the reaction is carried out in the presence of an inert solvent.

* * * * *

UNITED STATES PATENT AND TRADEMARK OFFICE
CERTIFICATE OF CORRECTION

PATENT NO. : 4,744,827

DATED : May 17, 1988

INVENTOR(S) : Jens Winkel, et al

It is certified that error appears in the above-identified patent and that said Letters Patent is hereby corrected as shown below:

| | |
|---|---|
| Col. 5, line 9 | After "freon" insert --.-- |
| Col. 10, line 48, Col. 12, line 15 Col. 12, line 55 | Left side of formula delete " 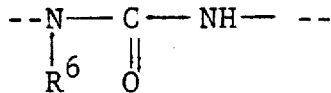 " and substitute -- 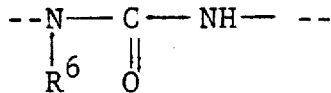 -- |
| Col. 10, line 54 | Delete "alkyoxy" and substitute --alkoxy-- |
| Col. 10, lines 54-55 | Correct spelling of --trifluoromethyl-- |
| Col. 12, line 31 and Col. 13, line 6 | Delete beginning of formula and substitute: |

$$--N-C-NH-- --$$
$$\phantom{--}|\phantom{-C-NH--}\|$$
$$\phantom{--}R^6\phantom{-}O$$

Signed and Sealed this

Tenth Day of January, 1989

Attest:

DONALD J. QUIGG

Attesting Officer

Commissioner of Patents and Trademarks